United States Patent [19]

Haddock et al.

[11] 4,102,671
[45] Jul. 25, 1978

[54] CONTROL OF WEEDS WITH N-SUBSTITUTED ALANINE COMPOUNDS

[75] Inventors: Ernest Haddock, Sheerness; Clive A. Raven; Alan J. Sampson, both of Sittingbourne, all of England

[73] Assignee: Shell Oil Company, Houston, Tex.

[21] Appl. No.: 819,014

[22] Filed: Jul. 25, 1977

Related U.S. Application Data

[62] Division of Ser. No. 709,756, Jul. 29, 1976.

[30] Foreign Application Priority Data

Jul. 29, 1975 [GB] United Kingdom ............... 31691/75

[51] Int. Cl.² .......................... A01N 9/12; A01N 9/20
[52] U.S. Cl. ......................................... 71/98; 71/111; 71/115
[58] Field of Search ........................... 71/98, 111, 115

[56] References Cited

U.S. PATENT DOCUMENTS

| | | | |
|---|---|---|---|
| 3,598,859 | 8/1971 | Yates et al. | 71/115 |
| 3,636,079 | 1/1972 | Koenig et al. | 71/111 X |
| 3,761,508 | 9/1973 | Haddock | 71/115 |
| 3,766,244 | 10/1973 | Giacobbe et al. | 71/115 X |
| 3,853,938 | 12/1974 | Haddock et al. | 71/100 |
| 3,994,713 | 11/1976 | Haddock et al. | 71/111 |

FOREIGN PATENT DOCUMENTS

| | | |
|---|---|---|
| 2,349,970 | 4/1974 | Fed. Rep. of Germany. |
| 2,504,319 | 8/1975 | Fed. Rep. of Germany. |
| 2,527,913 | 1/1976 | Fed. Rep. of Germany. |

*Primary Examiner*—Joseph Paul Brust

[57] ABSTRACT

Weeds are controlled by N-substituted alanine compounds of the general formula:

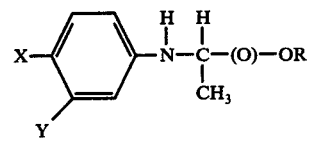

wherein the symbols have defined meanings.

4 Claims, No Drawings

CONTROL OF WEEDS WITH N-SUBSTITUTED ALANINE COMPOUNDS

This is a division, of application Ser. No. 709,756, filed July 29, 1976.

DESCRIPTION OF THE INVENTION

It has been found that useful herbicidal properties are possessed by N-substituted alanine compounds of the formula:

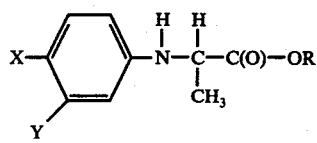

wherein X is chlorine or fluorine, Y is hydrogen, chlorine or fluorine, and R is hydrogen, alkyl of from one to six carbon atoms, and when R is hydrogen, the alkali metal, alkaline earth metal, ammonium, mono and dialkyl ammonium (in which each contains from one to six carbon atoms) and amine salts. The amine salts suitably are salts of amines commonly used to form amine salts of herbicidal compounds such as 2,4-D, 2,4,5-T and the like.

A preferred sub-genus of these herbicides consists of those of formula (I) wherein X is chlorine or fluorine, Y is chlorine and R is alkyl of from one to four carbon atoms, particularly methyl, ethyl or isopropyl.

Typical individual species of these herbicides are described in the examples set forth hereinafter. Other typical species include:

N-(3,4-dichlorophenyl)alanine, and the methyl, ethyl and isopropyl esters thereof;
N-(4-fluorophenyl)alanine and the ethyl ester thereof;
N-(3-chloro-4-fluorophenyl)alanine, ethyl ester;
N-(4-chloro-3-fluorophenyl)alanine, ethyl ester, isomers melting at 40°–42° and at 50°– ↑ °, respectively.

The alanine herbicides of the invention can exhibit optical isomerism. The invention includes the individual isomers, as well as mixtures thereof. It has been observed that in the majority of cases the dextro-rotatory isomer is more active herbicidally than the other isomer. Accordingly the dextro-rotatory isomers are preferred.

The herbicides of this invention are particularly effective when applied post-emergence -- i.e. to the foliage of -- broad-leaved plants. Since these herbicides have been found to be relatively non-toxic to grasses, they are of particular interest for controlling broad-leaved weeds in cereal crops -- particularly barley -- plantings.

The herbicides of this invention are known compounds, being disclosed in for example, U.S. Pat. Nos. 3,598,859, 3,761,508, 3,853,938 and 3,994,713, and German Pat. Nos. 2,349,970 (Offenlegungstag: Apr. 18, 1974) and 2,504,319 (Offenlegungstag: Aug. 7, 1975).

They can be prepared by conventional methods, e.g. by reaction of an aniline derivative of the formula:

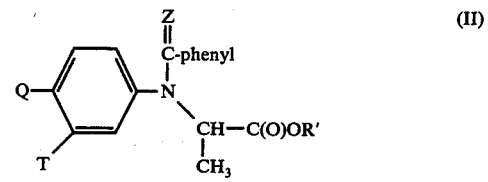

wherein X and Y are as defined above, with a propionic acid derivative of the formula:

$$CH_3-CH-C(O)OH$$
$$\phantom{CH_3-}|$$
$$\phantom{CH_3-}Cl$$

in the presence of a suitable base, for example, sodium bicarbonate, to absorb the hydrogen halide which is eliminated. The carboxylic acid product may then be esterified to give the required ester.

It has been found that the herbicidal spectrum of activity of the compounds of formula (I) can be remarkably extended by combining them with compounds of the formula:

(II)

wherein Z is oxygen or sulfur, Q is chlorine or fluorine, T is hydrogen, chlorine or fluorine and R' has the same meaning as does the symbol R, formula (I), already set out herein. These compounds are known to be effective selective herbicides for controlling wild oat plants in cereal grain plantings.

Surprisingly, although the compounds of formula (I) have essentially no activity against grass-like weeds, including wild oats, the combinations with compounds of formula (II) have enhanced activity with respect to wild oat plants, while the activity with respect to broad-leaved plants remains the same.

Accordingly, this invention includes combinations of one or more of the herbicides of formula (I) and one or more of the herbicides of formula (II). In these compositions the weight ratio of the compound of formula (I) to the compound of formula (II) suitably is within the range of from about 10:1 to about 1:10, with most effect being noted with combinations wherein the ratio lies within the range of from about 4:1 to about 1:2.

The herbicides of formula (II) also are known in the art, being disclosed in the patents which disclose the herbicides of formula (I), and also in German Pat. 2,527,913 (Offenlegungstag: Jan. 8, 1976)

A preferred subgenus of the herbicides of formula (II) consists of those species wherein Q and T each is chlorine or fluorine, Z is oxygen and R' is hydrogen or alkyl of from one to six carbon atoms, particularly methyl, ethyl, or isopropyl.

For use in controlling wild oats in barley plantings a preferred individual species of the genus of formula (II) is that wherein Q is fluorine T is chlorine, and Z is oxygen and R' is isopropyl.

For use in controlling wild oats in wheat plantings, a preferred subgenus consists of the compounds of formula (II) wherein Q is chlorine or fluorine, Z is chlorine and R' is methyl or ethyl.

As in the case of the herbicides of formula (I), the herbicides of formula (II) can exist in optically active forms, and, generally speaking, the laevo-rotatory form is the herbicidally most active form. Thus, where it is appropriate, the herbicide of formula (II) may be employed in its most active optically-active form, in combination with a herbicide of formula (I).

A particularly preferred herbicidal combination for the control of broad-leaved weeds and wild oats is one in which a herbicide of the genus defined in formula (I) is present in the dextro-rotatory form and the herbicide of the genus defined in formula (II) is present in the laevorotatory form.

From the foregoing discussion, it will be seen that the invention includes:
(a) use of an effective amount of one or more of the compounds of formula (I) for controlling unwanted broad-leaved plants;
(b) use of an effective amount of a combination of one or more of the compounds of formula (II) for controlling unwanted broad-leaved plants and wild oats in cereal grain plantings;
(c) as novel compositions of matter, one or more herbicides of formula (I) together with a carrier and/or surface-active agent;
(d) as novel herbicidal compositions of matter the combinations of an effective amount of one or more of formula (I) compounds with an effective amount of one or more formula (II) compounds, together with a carrier and/or surface active agent.

The uses (a) and (b) are embodied in methods which comprise spraying the foliage of the unwanted plants with an effective amount of the formula (I) compound(s) or the combination of formula (I) and formula (II) compounds.

For application, the herbicides of formula (I) and the combinations of formula (I) and formula (II) herbicides are formulated with other materials to facilitate application of the herbicide(s) to the foliage of the plants to be controlled, these materials being a carrier or a surfactant, or both.

In the following discussion of the manner in which herbicides of this invention can be formulated, in the interest of brevity, the term "herbicide" includes both the formula (I) herbicides and combinations of formula (I) and formula (II) herbicides.

The term "carrier" as used herein means a material which may be inorganic or organic and of synthetic or natural origin, with which the herbicide is mixed or formulated to facilitate its application to the plant to be treated, or its storage, transport, or handling. The carrier may be solid or a fluid. Any of the materials usually applied in formulating herbicides may be used as carrier.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulphate; synthetic hydrated silicon oxides and synthetic calcium or aluminum silicates; elements, such as for example, carbon and sulphur; natural and synthetic resins, such as for example, coumarone resins, rosin, copal, dammar, polyvinyl chloride and styrene polymers and copylmers; solid polychlorophenols; bitulen; waxes, such as for example, beeswax, paraffin wax, montan wax, and chlorinated mineral waxes; and solid fertilizers, for example, superphosphates.

Examples of suitable fluid carriers are water, alcohols, such as for example, isopropanol and glycols; ketones, such as for example, acetone, methyl ethyl ketone, methyl isobutyl ketone and cyclohexanone; ethers; aromatic hydrocarbons, such as for example, benzene, toluene and xylene; petrolum fractions, such as for example, kerosene, light mineral oils, chlorinated hydrocarbons, such as for example, carbon tetrachloride, perchloroethylene, trichloroethane, including liquefied normally gaseous compounds. Mixtures of different liquids are also suitable.

In addition to a carrier, the present composition may also contain one or more surface active agents. Suitable surface actsve agents include emulsyifying agents, dispersing agents and wetting agents. They may be non-ionic or ionic. Any of the surface-active agents usually applied in formulating herbicides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphates, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols. Wettable powders are usually compounded to contain 25, 50 or 75% w of the herbicide and usually contain, in addition to solid carrier, 3–10% w of a dispersing agent and, where necessary, 0–10% w of stabilizer(s) and/or other additives such as penetrants or stickers. Dusts are usually formulated as a dust concentrate having similar composition to that of a wettable powder but without a dispersant, and are diluted in the field with further solid carrier to give a composition usually containing 0.5–10% w of herbicide. Granules are usually prepared to have a size between 10 and 100 BS mesh, and may be manufactured by agglomeration or impregnation techniques. Generally, granules will contain 0.5–25% w herbicide and 0–10% w of additives such as stabilizers, slow-release modifiers and binding agents. Emulsifiable concentrates usually contain, in addition to the solvent and, when necessary, co-solvent, 10–50% w/v herbicide, 2–20% w/v emulsifiers and 0–20% w/v emulsifiers of appropriate additives such as stabilizers, penetrants and corrosion inhibitors. Suspension concentrates are compounded so as to obtain a stable, non-sedimenting, flowable product and usually contain 10–75% w herbicide, 0.5–15% w of dispersing agents, and 0.1–10% w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

The compositions of the invention may contain other ingredients, for example, protective colloids such as gelatin, glue, casein, gums, cellulose ethers, and polyvinyl alcohol; thixotropic agents, e.g., bentonites, sodium polyphosphates; stabilizers such as ethylenediaminetetra-acetic acid, urea, triphenyl phosphate, and other herbicides or pesticides; and stickers, for example, non volatile oils.

Aqueous dispersions and emulsions, for example, compositions obtained by diluting a wettable powder or an emulsifiable concentrate according to the invention with water, also lie within the scope of the present invention. The said emulsions may be of the water-in-oil or of the oil-in-water type, and may have a thick mayonnaise-like consistency.

The amount of the herbicide necessary to control the unwanted plants will vary with the individual herbicide or combinations of herbicides used, the type of formulation, the age and condition of the plants, environmental conditions and other variable factors which must be and are taken into account by practitioners of the art of chemical control of unwanted plants. Recommendation as to precise dosages therefore is not possible. In general, however, dosages of from about 0.1 to 10 pounds per acre of the active ingredient(s) will be satisfactory. When applied to cereal grain plantings to control wild oats therein, the herbicides of the invention cause at most but minor injury to crop plants at the dosages which effectively control wild oats. However, it will be found to be preferable to use the minimum dosage required to effectively control the wild oats, to minimize the possibility of injuring the crop plants significantly. Liquid and dust formulations for such application ordinarily contain from about ½ to about 10% of the active ingredient(s).

Practice of the methods, including use of compositions of the invention, is illustrated in the following examples:

EXAMPLE 1

Demonstration of herbicidal activity of compounds of formula (I)

To demonstrate their herbicidal activity against broad-leaved weeds, compositions according to the invention were tested as foliar sprays on seedling plants of the following species; linseed, *Linum usitatissimun* (L); mustard, *Sinapis alba* (M); sugar beet, *Beta vulgaris* (SS); and soya bean, *Glycine max* (S).

The formulations used in the test were prepared by diluting with water solutions of the compounds in acetone containing 0.4% by weight of an alkylphenol ethylene oxide condensate available under the trade name Triton X-155. The acetone solutions were diluted with an equal volume of water and the resulting formulations applied at four dosage levels corresponding to 0.1, 0.3, 1.0 or 3.0 kilograms of active material per hectare. There were 3 replicates of each treatment. Phytotoxicity was assessed visually 12 to 14 days after spraying the foliage, on the standard 0-9 scale. These phytotoxicity scores were submitted for probit analysis to calculate the growth inhibition dosages in kg/ha required to give a 50% reduction (G I D). The results are summarized on Table 1.

Table 1

| Compound | L $GID_{50}$ | M $GID_{50}$ | SB $GID_{50}$ | S $GID_{50}$ |
|---|---|---|---|---|
| N-(3-Chloro-4-fluorophenyl)alanine methyl ester (racemic mixture) | 0.43 | 0.70 | 0.77 | 0.71 |
| N-(3-chloro-4-fluorophenyl)alanine methyl ester (+ isomer) | 0.18 | 0.30 | 0.44 | 0.45 |
| N-(3,4-dichlorophenyl)alanine ethyl ester (racemic mixture) | 0.51 | 0.36 | 0.73 | 0.14 |
| N-(3,4-dichlorophenyl)alanine ethyl ester (+ isomer) | 0.28 | 0.25 | 0.46 | 0.12 |
| N-(3-chloro-4-fluorophenyl) alanine | 0.51 | 0.41 | 1.1 | 0.75 |
| Methyl 2-(3-chloro-4-fluorophenyl) amino-3-methoxy propionate | 1.1 | 2.4 | 1.7 | 0.67 |

These figures also demonstrate that for a given compound the dextro-rotatory form is more herbicidally active than the racemic mixture.

EXAMPLE 2

Further demostration of herbicidal activity of compounds of formula (I)

A second series of compounds were applied as foliar sprays to soya bean at the cotyledon stage using the procedure described in example 1 and applying four dosage levels corresponding to 0.3, 0.6, 1.2 or 2.4 kilograms of active material per hectare. Phytotoxicity was assessed 16 days after spraying and the G I $D_{50}$ calculated. The results are summarized in Table 2;

Table 2

| Compound | S $GID_{50}$ |
|---|---|
| N-(3,4-dichlorophenyl)alanine isopropyl ester (dextro-rotatory isomer) | 0.12 |
| N-(3,4-dichlorophenyl)alanine ethyl ester (dextro-rotatory isomer) | 0.07 |
| N-(3-chloro-4-fluorophenyl)alanine isopropyl ester (dextro-rotatory isomer) | 0.60 |
| N-(3-chloro-4-fluorophenyl)alanine methyl ester (dextro-rotatory isomer) | 0.80 |

EXAMPLE 3

Demostration of selective herbicidal activity compounds of formula (I)

To demonstrate their selective herbicidal action (in controlling the growth of broad-leaved weeds in barley crops) the compositions according to the invention were tested as foliar sprays on seedling plants of the following species; mustard, *Sinapis alba* (M); soya bean, *Glycine max* (S); convolvulus, *Ipomea purpurea* (I) and barley, *Hordeum vulgare* (B).

The formulations used in the test were prepared as in Example I. Two tests were carried out.

TEST 1

The compounds were applied post-emergence to soya bean, mustard and barley at 4 dosages: barley from 3 to 24 kg/ha; soya beam and mustard from 0.2 to 1.6 kg/ha. There were 4 replicates of each treatment. Phytotoxicity was assessed visually on the standard 0-9 scale, 8 days after spraying. This data was analyzed by computer to calculate the growth inhibition dosages required to give a 50% reduction for barley, soya bean and mustard. The results are summarized in Table 3.

Table 3

| Compound | B GID$_{50}$ | S GID$_{50}$ | M GID$_{50}$ |
|---|---|---|---|
| N-(3-chloro-4-fluorophenyl) alanine | >20 | 2.89 | 0.69 |
| N-(3-chloro-4-fluorophenyl) alanine methyl ester (racemic mixture) | 16.3 | 0.93 | 0.65 |

TEST 2

The compounds were applied to soya bean, convolvulus and barley at 4 dosages; barley from 4 to 32 kg/ha and soya bean and convolvulus from 0.3 to 2.4 kg/ha. There were 3 replicates of each treatment. Phytotoxicity was assessed visually on the standard 0-9 scale 14 days (for barley) and 22 days (for soya bean and convolvulus) after spraying. The G I D$_{50}$'s obtained from this data are shown in Table 4.

Table 4

| Compound | B GID$_{50}$ | S GID$_{50}$ | I GID$_{50}$ |
|---|---|---|---|
| N-(3-chloro-4-fluorophenyl)alanine isopropyl ester (racemic mixture) | 11.7 | 1.28 | 1.60 |
| N-(3-chloro-4-fluorophenyl)alanine isopropyl ester (+ isomer) | 11.2 | 0.92 | 0.98 |

EXAMPLE 4

Demonstration of herbicidal activity of combinations of compounds of formula (I) and compounds of formula (II)

The combinations under test in this example were as follows: Mixture 1 N-benzoyl-N(3,4-dichlorophenyl-)alanine ethyl ester (A) and N-(3-4-dichlorophenyl)alanine ethyl ester (B). Mixture 2 N-benzoyl-N-(3-chloro-4-fluorophenyl)alanine methyl ester (C) and N-(3-chloro-4-fluorophenyl)alanine methyl ester (D). Mixture 3 N-benzoyl-N-(3-chloro-4-fluorophenyl)alanine methyl ester (C) and N-(3-chloro-4-fluorophenyl)alanine (E). Mixture 4 N-benzoyl-N-(3-chloro-4-fluorophenyl)alanine methyl ester (− isomer) (F) and N-(3-chloro-4-fluorophenyl)alanine methyl ester (+ isomer) (G). Mixture 5 N-benzoyl-N-(3-chloro-4-fluorophenyl-)alanine methyl ester (− isomer) (F) and N-(3,4-dichlorophenyl)alanine ethyl ester (+ isomer) (H). All compounds were formulated as 15-20% emulsifiable concentrates. The dosages used for compound (A) were 0.04, 0.08, 0.16 and 0.32 kg/ha and for compounds (C) and (F) 0.02, 0.04, 0.08 and 0.16 kg/ha. Sufficient amounts of the five compounds, B, D, E, G, and H, were added to produce mixtures with the required ratios. These five compounds were also applied alone at high dosages and were found to be inactive against cultivated oats at the dosages given in the test.

A number of 7 cm pots of John Innes No. 1 Compost were sown with 25-30 seeds of cultivated oats (*Avena sativa*). When the plants had reached the 1 - 1½ leaf stage, mixtures of different ratios of the compounds were sprayed using a logarithmic sprayer. Assessments were made 10 to 15 days after spraying according to the mixture. Phytotoxicity was assessed visually on a percentage scale (where 0 no effect and 100 no growth after spraying). The data was analyzed to calculate the growth inhibition dosages in kg/ha required to give a 90% reduction for oat (C I D$_{90}$). Results of these mixture tests are summarized in Table 5.

Table 5

| Mixture compound ratio A : B | GID$_{90}$ oats | Mixture compound ratio C : D | GID$_{90}$ oats | Mixture compound ratio C : E | GID$_{90}$ oats | Mixture 4 compound ratio F : G | GID$_{90}$ | Mixture 5 compound ratio F : H | GID$_{90}$ oats |
|---|---|---|---|---|---|---|---|---|---|
| 1 : 0 | 0.17 | 1 : 0 | 0.073 | 1 : 0 | 0.14 | 1 : 0 | >0.16 | 1 : 0 | >0.16 |
| 2 : 1 | 0.12 | 1 : 1 | 0.063 | 1 : 1 | 0.12 | 2 : 1 | 0.11 | 2 : 1 | 0.08 |
| 1 : 1 | 0.14 | 1 : 2 | 0.051 | 1 : 2 | 0.09 | 1 : 1 | 0.05 | 1 : 1 | 0.06 |
| 1 : 2 | 0.14 | 1 : 4 | 0.058 | 1 : 4 | 0.10 | 1 : 2 | 0.05 | 1 : 2 | 0.05 |
| 1 : 4 | 0.12 | 1 : 8 | 0.048 | 0 : 1 | — | 1 : 4 | 0.04 | 1 : 4 | 0.03 |
| 0 : 1 | — | 0 : 1 | — | | | 0 : 1 | — | 0 : 1 | — |

EXAMPLE 5

Further demonstration of herbicidal activity of combinations of compounds of formula (I) and compounds of formula (II).

The combinations under test in this example were as follows: N-thiobenzoyl N-(3-chloro-4-fluorophenyl)alanine isopropyl ester (A) and N-(3-chloro-4-fluorophenyl)alanine isopropyl ester (B).

The test procedure was the same as that given in Example 4. The dosages used for compound (A) were 0.24, 0.48, and 0.96 kg/ha with sufficient amounts of compound L added to give mixtures with the required ratios. Visual assessments were made 19 days after spraying and G I D$_{90}$ calculated as for previous tests.

Results of the test are given in Table 6.

Table 6

| Compound ratio A : B | GID$_{90}$ oat |
|---|---|
| 1 : 0 | 0.99 |
| 1 : 1 | 0.91 |
| 1 : 2 | 0.73 |
| 1 : 4 | 0.60 |
| 0 : 1 | |

We claim as our invention:

1. A herbicidally active composition which comprises a carrier, optionally a surface-active agent, and as active ingredients: (a) a compound of the formula:

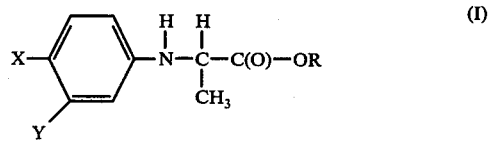

(I)

wherein X is chlorine of fluorine, Y is hydrogen, chlorine, or fluorine, and R is hydrogen, alkyl of from one to six carbon atoms, and when R is hydrogen, the alkali metal, alkaline earth metal, ammonium and mono- and di($C_1$-$C_6$-alkyl)ammonium salts thereof and (b) a compound of the formula:

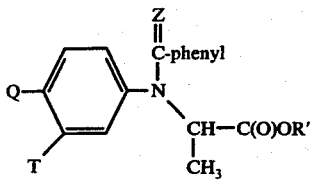

wherein Z is oxygen or sulfur, Q is chlorine or fluorine, T is hydrogen, chlorine or fluorine and R' represents one of the moieties represented by the symbol R, the weight ratio of the compound of formula (I) to the compound of formula (II) being within the range of from about 4:1 to about 1:2.

2. A composition according to claim 1 wherein Y is chlorine, R is alkyl of from one to four carbon atoms, Q and T each is chlorine or fluorine, Z is oxygen and R' is hydrogen or alkyl of from one to six carbon atoms.

3. A method for controlling broad-leaved plants and wild oat plants in cereal crop plantings which comprises applying to the foliage of the plants a herbicidally effective amount of a composition of claim 1.

4. A method for controlling broad-leaved plants and wild oat plants is cereal crop plantings which comprises applying to the foliage of the plants a herbicidally effective amount of a composition of claim 2.

* * * * *